United States Patent
Dearman

[11] Patent Number: 5,183,037
[45] Date of Patent: Feb. 2, 1993

[54] RESUSCITATOR VALVE

[75] Inventor: Peter T. Dearman, Bishop'Stortford, United Kingdom

[73] Assignee: Neotronics Medical Limited, Hertfordshire, England

[21] Appl. No.: 655,387

[22] PCT Filed: Aug. 17, 1989

[86] PCT No.: PCT/GB89/00957
§ 371 Date: Feb. 12, 1991
§ 102(e) Date: Feb. 12, 1991

[87] PCT Pub. No.: WO90/01965
PCT Pub. Date: Mar. 8, 1990

[30] Foreign Application Priority Data
Aug. 17, 1988 [GB] United Kingdom ............... 8819514

[51] Int. Cl.$^5$ ............................................. A61M 16/00
[52] U.S. Cl. .......................... 128/204.18; 128/205.24; 128/205.25
[58] Field of Search ............... 128/204.18, 204.21, 128/204.23, 204.26, 205.24, 205.25, 206.11, 203.11

[56] References Cited

U.S. PATENT DOCUMENTS

| | | | |
|---|---|---|---|
| 3,938,551 | 2/1976 | Henkin | 137/613 |
| 4,193,406 | 3/1980 | Jinotti | 128/204.18 |
| 4,592,349 | 6/1986 | Bird | 128/204.25 |
| 4,685,456 | 4/1987 | Smart | 128/205.25 |
| 4,705,073 | 11/1987 | Beck | 128/205.24 |
| 4,873,971 | 10/1989 | Perkins | 128/204.23 |
| 4,932,401 | 6/1990 | Perkins | 128/204.23 |
| 4,957,107 | 9/1990 | Sipin | 128/204.21 |
| 4,971,049 | 11/1990 | Rotariu et al. | 128/204.21 |
| 4,995,387 | 2/1991 | Jinotti | 128/205.24 |
| 5,005,571 | 4/1991 | Dietz | 128/206.11 |
| 5,018,519 | 5/1991 | Brown | 128/205.25 |
| 5,038,770 | 8/1991 | Perkins | 128/204.18 |
| 5,048,515 | 9/1991 | Sanso | 128/204.18 |

FOREIGN PATENT DOCUMENTS

| | | |
|---|---|---|
| 0190856 | 3/1991 | European Pat. Off. |
| 1205518 | 4/1958 | France . |
| 826280 | 3/1958 | United Kingdom . |

Primary Examiner—Edgar S. Burr
Assistant Examiner—Aaron J. Lewis
Attorney, Agent, or Firm—Kerkam, Stowell, Kondracki & Clarke

[57] ABSTRACT

A valve system is described by means of which air can be supplied to a patient either automatically, i.e. in pulses from a control module (19), or under manual control. The valve system has a housing (10) containing an outlet end (16) connected to a face mask (11), a first channel (24) connected to the control module (19) via an annular line (21) for supply of pulsed air to the mask and a second channel (32) connected to a steady source of air via a line 28 for supply of air under manual control to the face mask. A main valve member (33) is provided that can slide between a first position (as shown) that allows gas to pass down the first channel (24) to the mask and closes off the second channel (32) and a second position that allows gas to pass down the second channel (32) to the mask and closes off the first channel (24). In the second position of the main valve (33), the supply of air to the patient is controlled by a manually operable second valve member (62) in the second channel (32).

9 Claims, 4 Drawing Sheets ic resuscitating apparatuses are used to supply an oxygen-containing gas to a patient. Such apparatuses include a pressurised source of the oxygen-containing gas (which we shall refer to hereinafter simply as 'gas' and it may be air or air that has been enriched with oxygen or pure oxygen or indeed any other breathable oxygen-containing gas), a face mask and a control module which, when operating in an 'automatic' mode, feeds pulses of the gas to the face mask to inflate the patient's lungs. The control module may sense the pressure of the gas in the mask (or in a line leading to the mask) and provide a pulse of gas when the pressure has fallen to a predetermined value. At the end of each pulse the patient exhales (during which time no gas is supplied); at the end of exhalation, the pressure in the mask has fallen to or below the threshold value and so another pulse of gas is supplied by the control module.

However, particularly in the case of patients who have suffered a heart attack, such automatic supply of pulses of gas should not be used and instead the control module should be switched to a 'manual' mode of operation in which it provides a continuous supply of gas to a gas line containing a manually-operated valve or trigger; the valve controls the flow of gas in the gas supply line and can be closed to stop gas flow to allow the patient to exhale and opened to initiate flow again to inflate the patient's lungs.

Hitherto, a control module that is operable in both an automatic and a manual mode has required a separate face mask connected to a separate gas supply line for each mode of operation; thus, if the control module were being operated in the automatic mode supplying pulses of gas to a patient by way of the appropriate face mask and if it were then necessary to change over to manual control, the face mask and the supply line for the automatic mode of operation has to be taken off the patient and the mask and supply line for the manual mode of operation has to be fitted instead; simultaneously, it is necessary to switch the control module to supply a constant stream of gas to the second (manual) mask and to disconnect the source of gas to the first (automatic) mask. Since the control module may be out of easy reach of the medical personnel administering the resuscitation, the whole operation can be awkward, take vital time and interrupt the supply of gas to the patient and so, in an extreme case, could endanger the patient's life.

DISCLOSURE OF INVENTION

We have devised a system which overcomes the above problems by providing a single mask connected to receive gas from two supply lines, one line providing a continuous stream of gas for manual operation and the other providing a pulsed stream of gas from a control module for automatic operation; a valve is also provided that is capable of connecting one of the lines to the mask while shutting off the other line.

According to the present invention there is provided a resuscitation system comprising a first gas line, a control module capable of supplying a pulsed stream of pressurised gas to the first line, a second gas line, means capable of supplying a continuous stream of pressurised gas to the second line, a face mask, a main valve connected to both the first and the second lines and being capable of passing gas from either one of the lines to the mask and of closing the other gas line, and a second valve for manual control of the flow of gas along the second gas line when this is connected to the mask.

It is preferred that the main valve includes a single valve member that connects the desired gas line to the mask and simultaneously closes the gas line that is not desired.

The second gas line may receive the continuous stream of gas directly from a gas source, e.g. a compressed gas cylinder, or via the control module.

According to a second aspect of the present invention, there is provided a valve system for controlling the supply of gas to a face mask, which comprises a housing, a first gas channel having an inlet for connection to a source of pulsed gas from a control module and an outlet for connection to a face mask, a second gas channel having an inlet for connection to a source of pressurised gas and an outlet for connection to the said face mask, a manually controllable main valve member that is movable between a first position in which it closes the second channel and opens the first channel and a second position in which it closes the first channel and opens the second channel and wherein the valve system further includes a second manually controllable valve member that controls flow of gas through the second channel.

BRIEF DESCRIPTION OF DRAWINGS

The present invention will now be described by way of example only with reference to the accompanying drawings in which.

BEST MODE OF CARRYING OUT THE INVENTION

Figure 1:
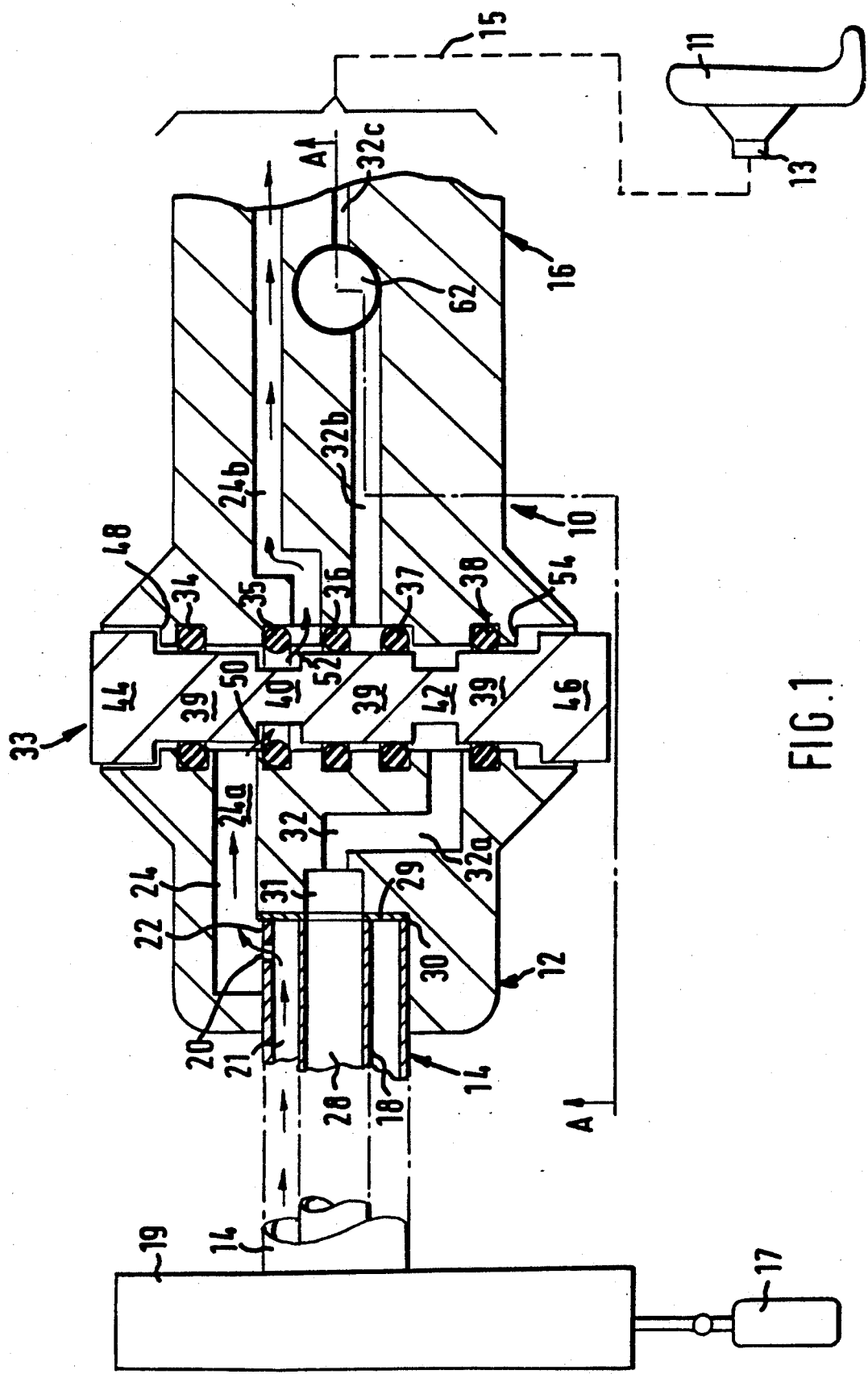
FIG. 1 is a longitudinal cross-sectional view through a valve system of the present invention in one position of operation and also shows a side view of a control unit, a source of compressed air, a patient valve and a face mask.

Referring to FIG. 1, the valve has a housing 10 having an inlet end 12 connected to a control module 19 (shown schematically) by a pipe 14 and a mask end 16 connected to a mask 11 by way of a patient valve 13; the end 16 is connected to the mask and patient valve either directly or via a length of pipe or tubing 15. The control module 19 receives compressed gas from a source which can for example be a gas cylinder 17 or a compressed gas line, and supplies this gas to pipe 14. The pipe 14 to the control module 19 includes an outer, annular line 21 connected to receive pulses of pressurised gas 17 from the control monitor 19 as determined by parameters in the patient valve 13, in the mask 11, in the pipe 15 or in the line 21 (as is known); this pulsed supply of gas is generally known as 'automatic' operation and we will refer to it as such. The control monitor 19 necessary for automatic control of the gas through line 21 is widely available commercially and so we will not describe it in further detail.

The pipe 14 has an outer wall 18 which has a hole 20 formed near one of its ends to allow gas from the annular line 21 to pass into an inlet 22 of a first ('automatic') gas flow channel 24 that extends through the housing 10 and that consists of two parts 24a and 24b. The pipe 14 also has an inner line 28 connected to the control monitor 19 (although it could be connected directly to the source of pressurised gas 17) to provide a continuous supply of gas down line 28, when required.

The end of the pipe 14 is held in the valve housing 10 by any known means, e.g. by a spring clip and/or by a screwthread, so that the end face 30 of the pipe 14 abuts a resilient washer 29 in the housing to provide a gas-tight seal. The inner line 28 is thus in direct communication with an inlet 31 of a second channel 32 which passes through the housing 10 and consists of three parts 32a, 32b and 32c as will be described in greater detail later.

A main valve member 33 is slidably disposed in the housing 10 to selectively close and open channels 24 and 32. In the position shown in FIG. 1 it selectively blocks the second ('manual') channel 32 and allows flow of gas down the first ('automatic') channel 24; 'O' rings 34 to 38 isolate the gas flow from the atmosphere and prevent gas from the two channels mixing and ensure that a closed channel is effectively blocked without leaks, The valve member 33 has central part 39 that is generally of uniform cylindrical cross-section but includes two cylindrical bypass sections 40 and 42 of reduced cross-section. The ends of the valve member 33 are formed by heads 44 and 46 of larger cross-section. In the position shown in FIG. 1, the valve member 33 has been pushed down until the head 44 abuts the wall of a recess 48 in the housing 10; in this position, a gap 50 is created between the top edge of the bypass 40 and the 'O' ring 35 and a further gap 52 is created between the bottom edge of bypass 49 and 'O' ring 35. These gaps allow gas to flow along channel 24 (as shown by arrows), from part 24a to part 24b and hence to the patient valve 13 and the face mask 11 so that the flow of gas to the mask is controlled in the automatic mode by the control module 19. It will be observed that in FIG. 1, the second channel 32 is blocked as a result of the valve member 33 abutting 'O' rings 37 and 38.

Figure 2:
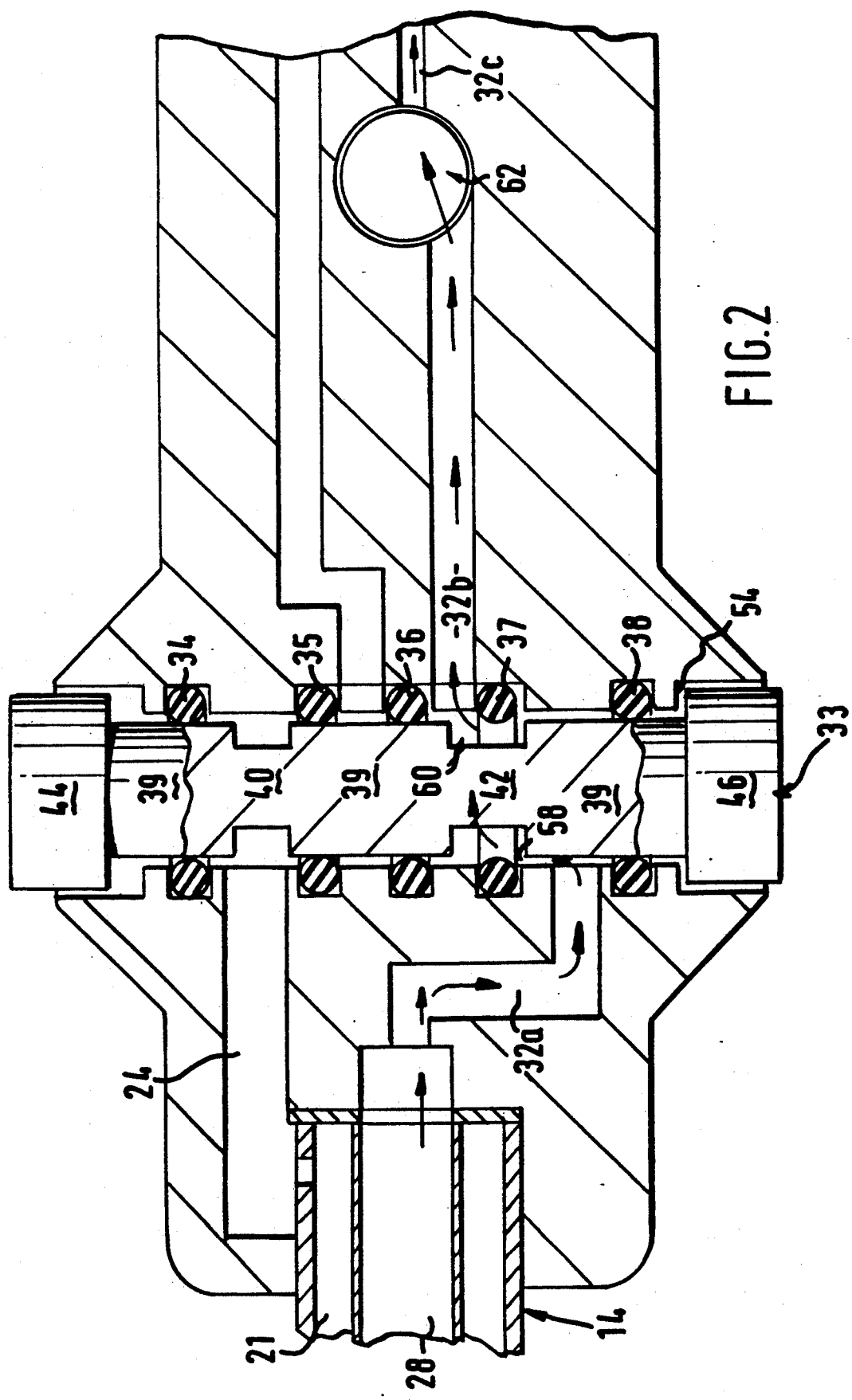
FIG. 2 is a longitudinal cross-sectional view through the valve system shown in FIG. 1 but in a second position of operation.

The valve member 33 can be moved from a position providing automatic control of gas (as shown in FIG. 1) to a position providing manual control (as shown in FIG. 2) by sliding the main valve 33 upwards until head 46 abuts the end of a recess 54 in the housing. In this position the 'O' ring 35 abuts the main control section 39 of the valve member 33 to eliminate gaps 50 and 52 (shown in FIG. 1) but gaps 58 and 60 are created between 'O' ring 37 and the edges of the bypass section 42 thereby allowing gas to pass from the first part 32a of the second channel to the second pat 32b so that gas can be supplied from the continuous uninterrupted source (in this case control monitor 19) along line 28 and through parts 32a and 32b of the second channel 32. Control of gas flow through channel 32 is achieved by a manually operated valve member 62 positioned at the end of channel part 32b and is shown in greater detail in FIGS. 3 and 4.

Figure 3:
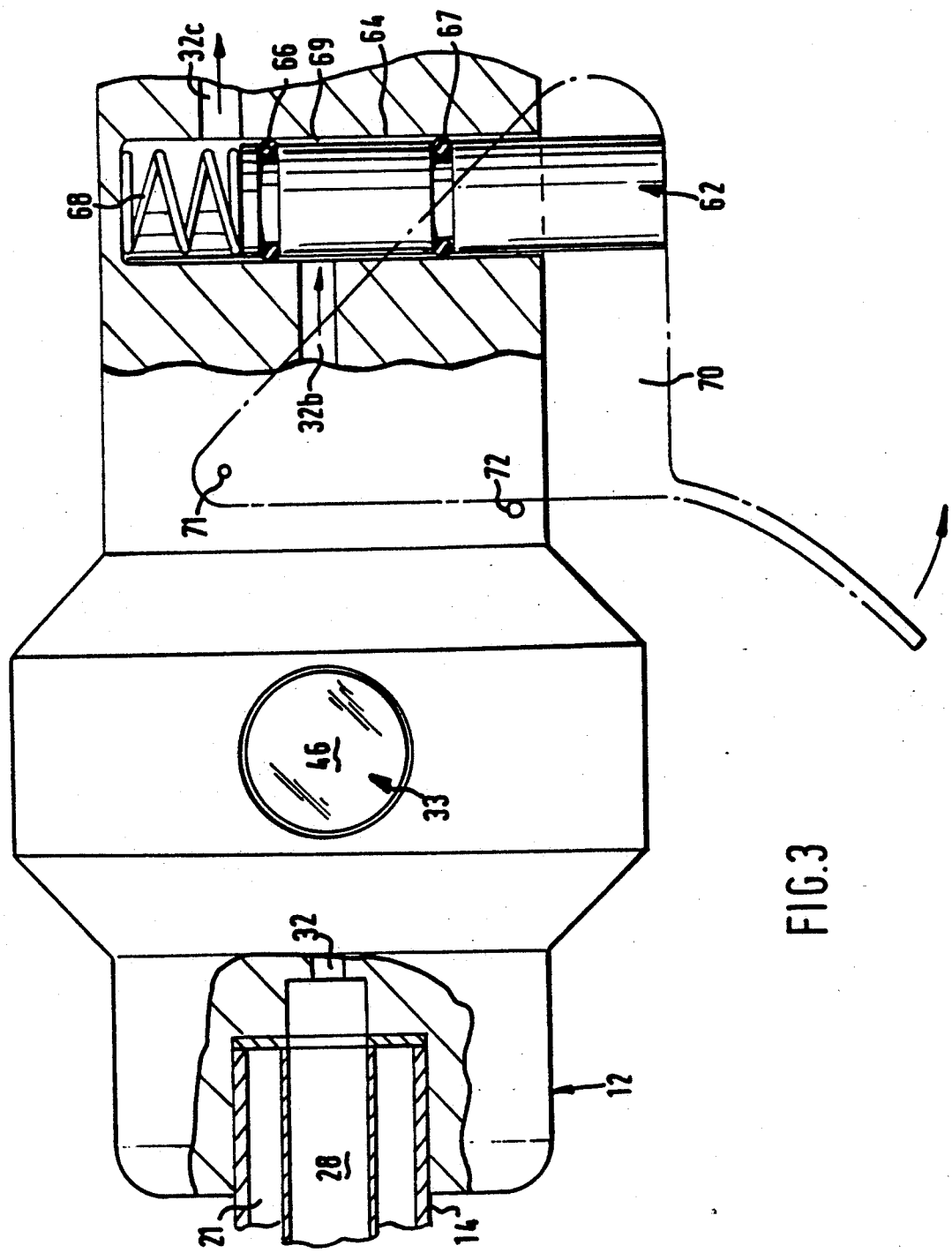
FIG. 3 is a part-sectional view along line A—A of FIG. 1, and is shown partly cut-away.
Figure 4:
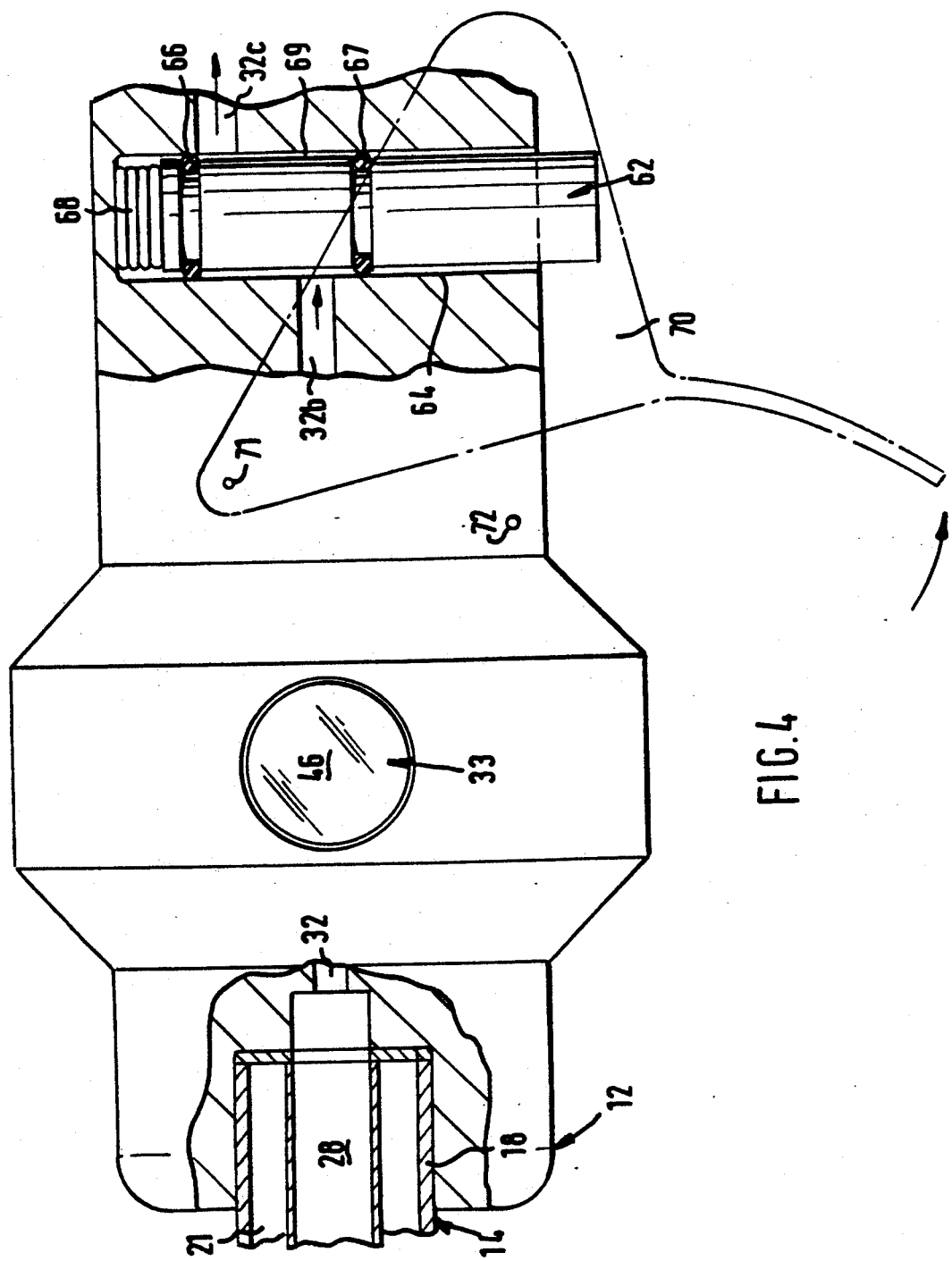
FIG. 4 is the same view as in FIG. 3 but in a different state of operation.

Referring now to FIGS. 3 and 4, the valve member 62 is slidable within a cylindrical bore 64 in the housing 10 and includes two 'O' rings 66 and 67 to provide seals between the member and the walls of the bore. A spring 68 biases the member into the position shown in FIG. 3 where the 'O' rings 66 and 67 seal off the end of channel 32b and prevent flow of gas through channel 32. A lever 70 can be pivoted about a pin 71 in an anticlockwise direction (as seen in FIG. 3) to move the member 62 further into the bore 64 against the action of spring 68 to a position shown in FIG. 4 in which gas can flow from channel part 32b, through a gap 69 between the member 62 and the bore wall 64 and out through outlet channel part 32c to the patient valve 13 and the face mask 11 (shown in FIG. 1). Channel part 32c can, if desired, merge with channel part 24b to form a single channel leading to the patient valve and the mask. The movement of the valve member 62 in the direction of the spring bias (i.e. out of the bore 64) is limited by a stop 72 which is engaged by lever 70. Thus, it can be seen that gas cannot flow through channel 32 during manual operation unless the lever 70 is operated.

Four automatic operation of the supply of gas to the face mask, the main valve member 33 is located in the position shown in FIG. 1 and the controlled gas flow provided by the control module 19 passes (as shown by the arrows) along line 21, through hole 20, into channel 24a, past valve member 33 (by way of gaps 50 and 52), into channel 24b and from there it passes to the patient valve 13 and the face mask 11. The main valve member 33 can be switched to manual control simply by sliding it up to the position shown in FIG. 2 and this blocks channel 24 and opens channel 32 so that gas can pass form line 28 of pipe 14, through channel 32a, past valve member 33 (by way of gaps 58 and 60), into channel 32b. However, control of the flow of gas through channel 32 is governed by the valve member 62 which can be opened when it is desired to supply gas to the patient by pivoting lever 70 to move valve member 62 into bore 64 against the action of spring 68 (allowing gas to flow into channel 32c and thence to the patient valve 13 and the mask 11); the valve member 62 can be closed when it is desired to stop the flow of gas to the mask to allow the patient to exhale by releasing the lever to allow the spring 68 to close the valve member 62.

It will be seen that a change over from an automatic to a manual mode of control (or vice versa) can be effected simply by moving slidable valve member 33, i.e. during the change over it is not necessary to remove the mask from the patient or to change the setting of the control module.

I claim:

1. A resuscitation system comprising a first gas line, a control module capable of supplying a pulsed stream of pressurised gas to the first line, a second gas line, means capable of supplying a continuous stream of pressurised gas to the second line, a face mask connected to receive gas from the first line and from the second line, a manually controllable main valve connected to both the first and the second lines and being capable of moving between a first position in which it closes the second line and opens the first line and a second position in which it closes the first line and opens the second line, and a second valve for manual control of the flow of gas along the second gas line when this is connected to supply gas to the mask.

2. A resuscitation system as claimed in claim 1, wherein the main valve is accommodated within a housing and wherein the second valve is included in the same housing.

3. A resuscitation system as claimed in claim 1, wherein the main valve includes a single valve member that connects the desired gas line to the mask and simultaneously closes the gas line that is not desired.

4. A resuscitation system as claimed in claim 3, wherein the main valve includes a housing and wherein the main valve member is slideable within a housing between a first position in which it allows the flow of gas through the first line and blocks the flow of gas through the second line and a second position in which it allows the flow of gas through the second line and blocks the flow of gas through the first line.

5. A resuscitation system as claimed in claim 1, wherein the second gas line is arranged to receive the continuous stream of gas directly from a gas source, e.g. a compressed gas cylinder, or via the control module.

6. A resuscitation system as claimed in claim 1, which includes a patient vale and wherein the main valve is arranged to supply gas to the mask via the patient valve.

7. A valve system for controlling the supply of gas to a face mask, which comprises a housing, a first gas channel having an inlet for connection to a source of pulsed gas from a control module and an outlet for connection to a face mask, a second gas channel having an inlet for connection to a source of pressurised gas and an outlet for connection to the said face mask, a manually controllable main valve member that is movable between a first position in which it closes the second channel and opens the first channel and a second position in which it closes the first channel and opens the second channel and wherein the valve system further includes a second manually controllable valve member that controls flow of gas through the second channel.

8. A valve system as claimed in claim 7, wherein the main valve member is slidable between the first and the second positions.

9. A resuscitation system comprising a first gas line, a control module capable of supplying a pulsed stream of pressurised gas to the first line, a second gas line, means capable of supplying a continuous stream of pressurised gas to the second line, a face mask, a main valve connected to both the first and the second lines and being capable of passing gas from either one of the lines to the mask and of closing the other gas line, and a second valve for manual control of the flow of gas along the second gas line when this is connected to the mask, said resuscitation system further comprising a housing containing both the main valve and the second valve, a first gas channel within the housing having an inlet connected to the first gas line and an outlet connected to the face mask, a second gas channel also contained within the housing and having an inlet connected to the second gas line and an outlet connected to the face mask, and wherein the main valve comprises a manually controllable valve member that is moveable between a first position in which it closes the second channel and opens the first channel and a second position in which it closes the first channel and opens the second channel and wherein the second valve comprises a second manually controllable valve member that controls flow of gas through the second channel.

* * * * *

UNITED STATES PATENT AND TRADEMARK OFFICE
CERTIFICATE OF CORRECTION

PATENT NO. : 5,183,037
DATED : Feb. 2, 1993
INVENTOR(S) : DEARMAN

It is certified that error appears in the above-identified patent and that said Letters Patent is hereby corrected as shown below:

Title page, item [75], inventor's address, "Bishop'" should be --Bishop's --.

Column 5, Claim 6, line 2 of claim, "vale" should be -- valve --.

Signed and Sealed this

Thirtieth Day of November, 1993

Attest:

BRUCE LEHMAN

*Attesting Officer*       *Commissioner of Patents and Trademarks*